(12) United States Patent
Haraguchi

(10) Patent No.: US 11,446,115 B2
(45) Date of Patent: Sep. 20, 2022

(54) MEDICAL DEVICE HOLDING APPARATUS

(71) Applicant: OLYMPUS CORPORATION, Tokyo (JP)

(72) Inventor: Masafumi Haraguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 932 days.

(21) Appl. No.: 16/238,981

(22) Filed: Jan. 3, 2019

(65) Prior Publication Data

US 2019/0133713 A1    May 9, 2019

Related U.S. Application Data

(63) Continuation of application No. PCT/JP2016/071131, filed on Jul. 19, 2016.

(51) Int. Cl.
*A61B 1/00* (2006.01)
*A61B 90/50* (2016.01)
(Continued)

(52) U.S. Cl.
CPC .......... *A61B 90/50* (2016.02); *A61B 1/00* (2013.01); *A61B 1/00149* (2013.01);
(Continued)

(58) Field of Classification Search
CPC ......... A61B 90/50; A61B 90/25; A61B 90/37; A61B 1/00; A61B 1/00149; A61B 1/3132; A61B 2090/504; A61B 2090/508
See application file for complete search history.

(56) References Cited

U.S. PATENT DOCUMENTS 5,658,238 A * 8/1997 Suzuki .............. A61B 1/00042
600/150
6,436,107 B1 * 8/2002 Wang ..................... A61B 34/75
606/139
(Continued)

FOREIGN PATENT DOCUMENTS

JP    H07-184926 A    7/1995
JP    H07-227398 A    8/1995
(Continued)

OTHER PUBLICATIONS

International Search Report dated Aug. 16, 2016 issued in PCT/JP2016/071131.

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A medical device holding apparatus having a first arm with a holding portion to hold a medical device; a second arm connected to the rotatable first arm; a base connected to the rotatable second arm and having a support shaft standing in a vertical direction; and a first counterweight portion connected to the second arm, wherein the second arm has a fulcrum around which the second arm is rotatable, and the first counterweight has a slit being connected to the proximal end portion of the second arm for guiding the proximal end portion of the second arm when the second arm is rotated around the fulcrum; and a guide for moving the first counterweight in the vertical direction after the guide receives a force generated when the proximal end portion of the second arm is guided and moved in the slit.

6 Claims, 9 Drawing Sheets

(51) Int. Cl.
    *A61B 1/313*     (2006.01)
    *A61B 90/25*     (2016.01)
    *A61B 90/00*     (2016.01)

(52) U.S. Cl.
    CPC ............ *A61B 1/3132* (2013.01); *A61B 90/25* (2016.02); *A61B 90/37* (2016.02); *A61B 2090/504* (2016.02); *A61B 2090/508* (2016.02)

(56) References Cited

U.S. PATENT DOCUMENTS

| | | | | |
|---|---|---|---|---|
| 6,786,896 | B1* | 9/2004 | Madhani | A61B 34/30 606/1 |
| 2001/0027313 | A1* | 10/2001 | Shimmura | A61B 90/50 606/1 |
| 2009/0187176 | A1* | 7/2009 | Assa | A61B 18/201 606/17 |
| 2009/0247819 | A1* | 10/2009 | Wilson | A61B 90/57 600/102 |
| 2009/0283647 | A1 | 11/2009 | Yasunaga et al. | |
| 2013/0140412 | A1 | 6/2013 | Hirose | |
| 2013/0296882 | A1* | 11/2013 | Kim | A61B 34/70 606/130 |
| 2018/0028269 | A1* | 2/2018 | Morel | A61B 34/76 |
| 2018/0289445 | A1* | 10/2018 | Krinninger | A61B 34/25 |

FOREIGN PATENT DOCUMENTS

| | | |
|---|---|---|
| JP | H07-289563 A | 11/1995 |
| JP | H08-140932 A | 6/1996 |
| JP | H08-233036 A | 9/1996 |
| JP | 2001-027346 A | 1/2001 |
| JP | 2001-120659 A | 5/2001 |
| JP | 2004-243136 A | 9/2004 |
| JP | 2006-230691 A | 9/2006 |
| JP | 2009-273714 A | 11/2009 |
| JP | 2012-000199 A | 1/2012 |
| JP | 5265818 B2 | 8/2013 |
| JP | 2015-188565 A | 11/2015 |

* cited by examiner

MEDICAL DEVICE HOLDING APPARATUS

BACKGROUND OF THE INVENTION

Field of the Invention

The present invention relates to a medical device holding apparatus and a suitable technology applied to the holding apparatus configured to maintain the medical device such as an endoscope and the like at an arbitrary position.

This application is a continuation application based on a PCT International Application No. PCT/JP2016/071131, filed on Jul. 19, 2016. The content of the PCT International Application is incorporated herein by reference.

Description of Related Art

The laparoscopic surgery using an endoscope is performed since it brings significant benefits to a patient at a view point of the postoperative recovery. During the laparoscopic surgery, a scope holder (holding apparatus) is frequently used in order to prevent a hand-shake of a scopist holding the endoscope and reduce the fatigue of the scopist. By using the scope holder, it is easy to change the position and the orientation of the scope.

As a result, it is possible to provide a good visual filed with less hand-shake and the surgeon can operate the scope by himself/herself so as to bring significant benefits to the surgery. A counter balance system is adopted in some scope holders to realize the operation control by a simple mechanism. This is because the function can be realized by a simple mechanism.

In Japanese Unexamined Patent Application, First Publication No. 2009-273714, an example of scope holder having a counterbalance mechanism configured to balance a position of a support target by a counterweight such that the support target supported by an arm can be freely moved by an arm using a less force. Here, the support target and the counterweight are rotated about a fulcrum as a rotation center such that the balance can always be kept.

In Japanese Unexamined Patent Application, First Publication No. 2015-188565, a scope holder having a balance mechanism configured to balance an arm by a winding constant force spring and an electromagnetic lock.

SUMMARY OF THE INVENTION

According to a first aspect of the present invention, a medical device holding apparatus has a first arm mechanism having a holding portion configured to hold a medical device; a second arm mechanism connected to the first arm mechanism so as to make the first arm mechanism to be rotatable; a base connected to the second arm mechanism so as to make the second arm mechanism to be rotatable, the base having a support shaft standing in a vertical direction; and a first counterweight portion connected to a proximal end portion of the second arm mechanism, wherein the second arm mechanism has a fulcrum connected to the support shaft, the second arm mechanism being rotatable around the fulcrum, and wherein the first counterweight has: a slit connected to the proximal end portion of the second arm mechanism, the slit being configured to guide the proximal end portion of the second arm mechanism when the second arm mechanism is rotated around the fulcrum; and a guide configured to move the first counterweight in the vertical direction after the guide receives a force generated when the proximal end portion of the second arm mechanism is guided and moved in the slit.

According to a second aspect of the present invention, in the medical device holding apparatus according to the first aspect, the slit may be formed in a downward convex curved shape.

According to a third aspect of the present invention, the medical device holding apparatus according to the first aspect may further include a second counterweight different with the first counterweight, the second arm mechanism may have a first arm having a distal end connected to the first arm mechanism and a proximal end connected to the first counterweight portion; a second arm disposed parallelly to the first arm; a third arm having a distal end connected to the first arm and a proximal end connected to the second counterweight portion, the third arm being connected to the second arm; and a fourth arm having a distal end connected to the first arm and a proximal end connected to the second arm, the fourth arm being parallel to the third arm.

According to a fourth aspect of the present invention, in the medical device holding apparatus according to the first aspect, the fulcrum may have a brake mechanism configured to suppress rotation of the second arm mechanism.

According to a fifth aspect of the present invention, the medical device holding apparatus according to the fourth aspect may further have a spring configured to bias the first counterweight portion downward in the vertical direction, wherein the shape of the slit is determined such that a bias force of the spring, a rotation-suppressing force of the brake mechanism with respect to the second arm mechanism, and a force generated at the slit when the slit guides the proximal end portion of the second arm mechanism are balanced.

According to a sixth aspect of the present invention, in the medical device holding apparatus according to the first aspect, the proximal end portion of the second arm mechanism may have a contacting portion, the contacting portion contacting with the slit in a point-contact manner in a guide direction in which the proximal portion of the second arm mechanism is guided.

DETAILED DESCRIPTION OF THE INVENTION

First Embodiment

Hereinafter, a medical device holding apparatus according to a first embodiment of the present invention will be described according to the figures.

Figure 1:
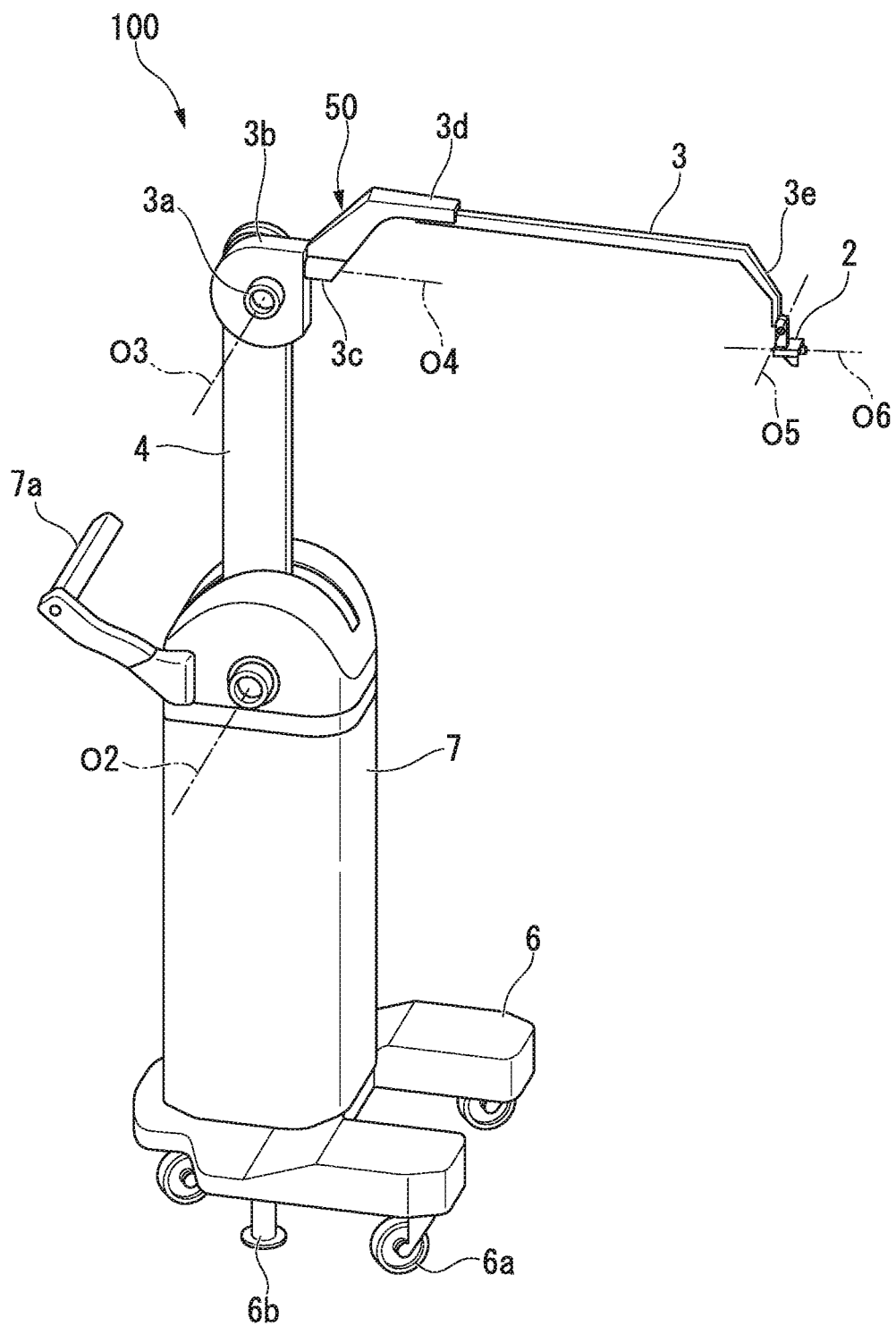
FIG. 1 is a perspective view showing a medical device holding apparatus according to a first embodiment of the present invention.
Figure 2:
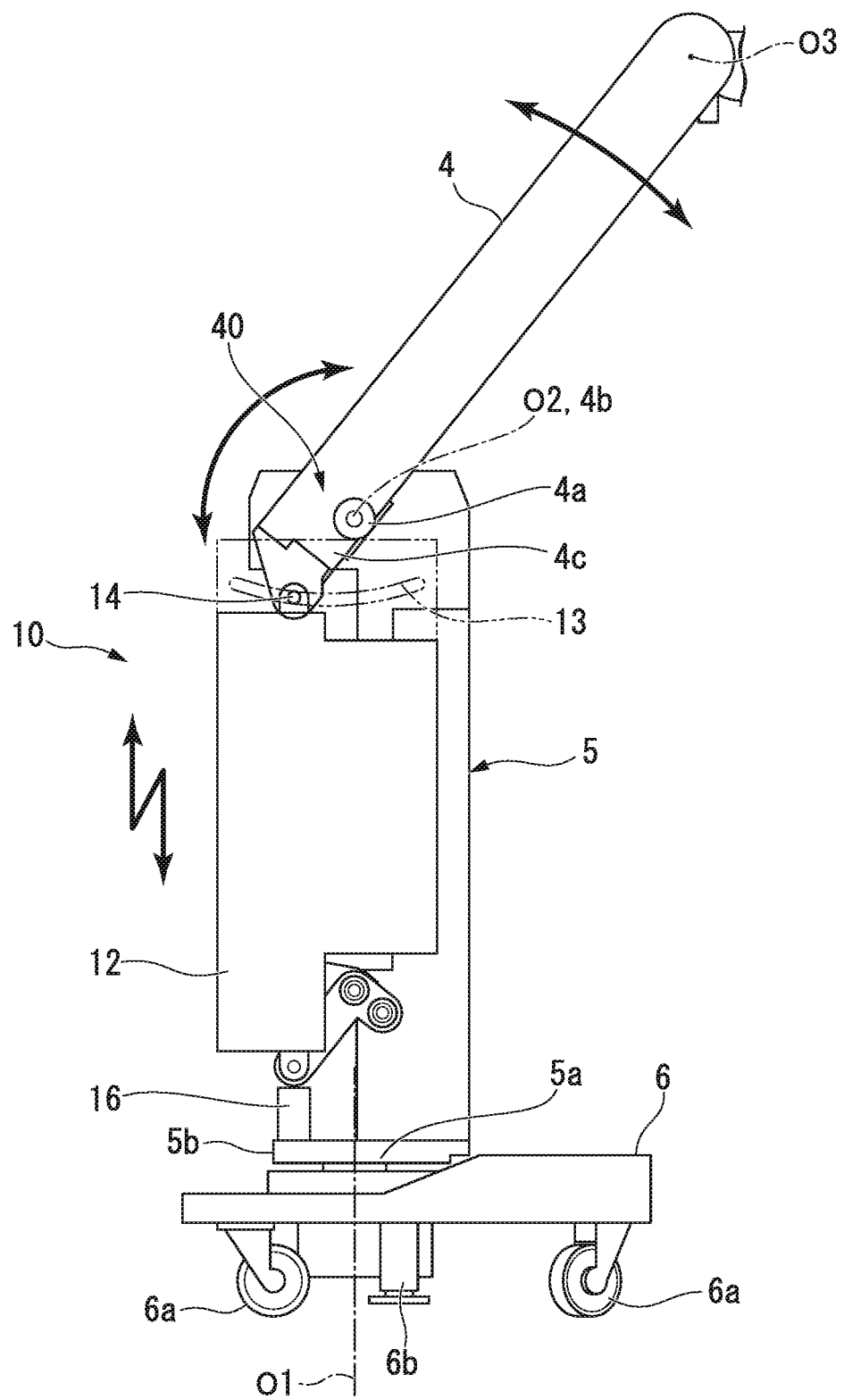
FIG. 2 is a front view showing a counterbalance mechanism of the medical device holding apparatus according to the present embodiment.

FIG. 1 is a perspective view showing a medical device holding apparatus according to the present embodiment, and FIG. 2 is a front view showing a counterbalance mechanism of the medical device holding apparatus according to the present embodiment in which a part of the configuration is seen through. In the figures, the medical device holding apparatus is shown as the numeral 100.

The medical device holding apparatus 100 according to the present embodiment is arranged in an operating room, a laboratory, a treating room and the like. The medical device holding apparatus 100 is configured to hold a medical device such as a microscope, an endoscope, a medical treatment tool, a medical display apparatus and the like. The medical device holding apparatus 100 is configured for fully brining out functions of the medical device while reducing fatigue of a surgeon such as a physician and the like as long as possible by making a position of the medical device to be freely movable in in a three dimensional space regardless of the surrounding environment.

As shown in FIGS. 1 and 2, the medical device holding apparatus 100 has a first arm mechanism 3, a second arm mechanism 4, a base 6, and a counterbalance mechanism 10. The first arm mechanism 3 has a holding portion 2 at a distal end thereof for holding the medical device. The second arm mechanism 4 has a distal end connected to a proximal end of the first arm mechanism 3 so as to make the proximal end of the first arm mechanism 3 to be rotatable. The base 6 is connected to the second arm mechanism 4 such that the second arm mechanism 4 is rotatable and the base 6 has a support shaft 5 standing in a vertical direction. The counterbalance mechanism 10 is configured for freely moving the medical device in a perpendicular direction and in a horizontal direction.

The proximal end side of the second arm mechanism 4, the counterbalance mechanism 10, and the support shaft 5 are accommodated in a cover portion 7 which is formed in a tubular shape standing in the vertical direction on the base 6.

A plurality of casters 6a are arranged on a bottom surface of the base 6 so as to be movable. It is possible to arrange a foot pedal 6b in the base 6 which is used as a suitable braking means or a fixing means for stopping rotations of the plurality of casters 6a or a movement of the base 6 with respect to the floor.

At an upper side of the cover portion 7, a grasping portion 7a is arranged for being grasped when the medical device holding apparatus 100 is moved.

A bearing portion 5a is arranged in the base 6 and a lower end of a support arm (support shaft) 5 is supported by the bearing portion 5a, wherein the support arm 5 is freely rotatable around a vertical axis O1 with respect to the base 6.

The support shaft 5 extends along the vertical axis (axis) O1. At the upper side of the support shaft 5, a rotation axis (horizontal axis) O2 orthogonal to the vertical axis O1 is arranged in the horizontal direction, and an arm (second arm mechanism) 4 is attached to the distal end of the support shaft 5 wherein the arm 4 is freely rotatable (swinging) around the rotation axis O2 via a bearing portion 4a.

The support shaft 5 is rotatable with respect to the base 6, and the support shaft 5 is rotatable with respect to the base 6 by the rotation-force adjustment portion 5b. At this time, the horizontal axis O2 is preferable to be positioned intersecting with the vertical axis O1.

The proximal end side of to the second arm mechanism 4 is supported by the distal end side of the support shaft 5 so as to be freely rotatable around the horizontal axis O2 as a center at the bearing portion 4a as a fulcrum 4b. The distal end of the second arm mechanism 4 is connected with the first arm mechanism 3 such that the first arm mechanism 3 is rotatable around a horizontal axis O3 parallel to the horizontal axis (axis) O2 and being through a bearing portion 3a.

A balance member 4c is connected to the proximal end side of the second arm mechanism 4 such that the balance member 4c is positioned at a position more proximal than the bearing portion 4a on an extension in the axial direction of the second arm mechanism 4. As described below, a contacting portion 14 is disposed in the balance member 4c wherein the contacting portion 14 is configured to come in contact with a counterweight portion 12 to keep balance. The bearing portion 4a configured as the fulcrum 4b has a braking mechanism 40 for suppressing the rotation of the second arm mechanism 4 around the horizontal axis O2. The braking mechanism 40 will be described below.

The first arm mechanism 3 has a rotation portion 3b, a first extension portion 3d, and a second extension portion 3e. At the proximal end side of the first arm mechanism 3, the rotation portion 3b is supported by the distal end side of the second arm mechanism 4 via the bearing portion 3a such that the rotation portion 3b is rotatable around the horizontal axis (axis) O3 as the center, wherein the horizontal axis O3 is parallel to the horizontal axis O2. The first extension portion 3d is bent in a radial direction of an axis O4 in which the first arm mechanism 3 extends such that the first extension portion 3d is rotatable around the axis O4 as the center with respect to the rotation portion 3b via the bearing portion 3c. The second extension portion 3e is arranged at the distal end side of the first arm mechanism 3 and the second extension portion 3e is bent in the radial direction of the axis O4 so as to extend to a position coincide with the axis O4. As the same with the bearing portion 4a of the second arm mechanism 4 described below, the braking mechanism 40 can be provided at the bearing portion 3a for suppressing the rotation of the first arm mechanism 3 around the horizontal axis O3. As described below, a braking mechanism 50 can be provided at the bearing portion 3c for suppressing the rotations of the first extension portion 3d and the second extension portion 3e in the first arm mechanism 3 around the axis O4.

Due to the first extension portion 3d and the second extension portion 3e, the first arm mechanism 3 is configured to extend parallely to the axis O4 while the first arm mechanism 3 can rotate around the axis O4 in this state. Accordingly, even if the first arm mechanism 3 is rotated around the axis O4, the position of the medical device such as the endoscope and the like does not change and the view field by the endoscope does not change. Also, collisions between the first arm mechanism 3 and the surgeon, the assistance, or the devices around the forceps can be avoided such that it is easy to secure a workspace without changing the location of the whole medical device holding apparatus 100.

At the distal end side of the first arm mechanism 3, a cylindrical holding portion 2 is attached thereto via the second extension portion 3e. The medical device such as the endoscope and the like can be fixed inside an inner aperture of the holding portion 2.

The holding portion 2 together with the medical device can rotate around the axis O4 of the first arm mechanism 3 and axes O5 and O6 which are orthogonal to each other and crossing at a common point on the axis O4 as center axes, and the rotation force necessary for the rotation can be adjusted by a rotation-force adjustment portion. It is preferable that the center axes O4, O5, and O6 are arranged to be orthogonal to each other. Also, it is preferable that the holding portion 2 is configured to be capable of definitely fixing the medical device at a necessary axial position and a rotation position when the medical device is moved along the axis O6 and rotated around the axis O6.

In this way, by arranging the mechanism which can tilt the holding portion 2 in 3-axis directions at the first arm mechanism 3, it is possible to adjust both of the arranging position and the orientation of the medical device held by the holding portion 2 in various ways. Particularly, in a situation that the medical device is at least one of the microscope, the endoscope, the medical display apparatus, and the medical treatment tool, accurate position and orientation control can be performed to fully bring out functions of the medical devices.

Figure 3:
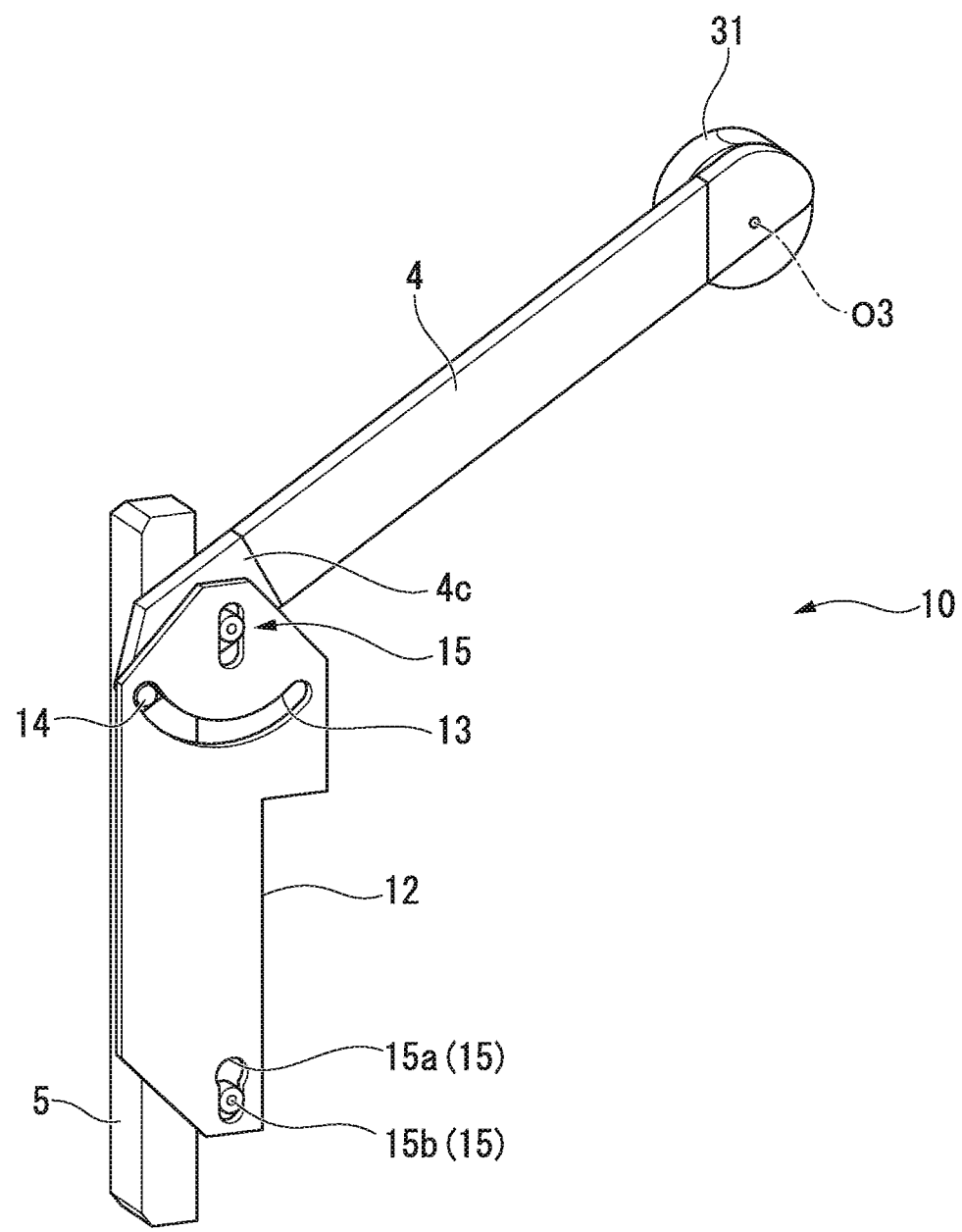
FIG. 3 is a perspective view showing an operation of the counterbalance mechanism of the medical device holding apparatus according to the present embodiment.

FIG. 3 is a perspective view showing a counterbalance mechanism 10 of the medial device holding apparatus 100 according to the present embodiment.

As shown in FIGS. 1-3, the counterbalance mechanism 10 has a first counterweight portion 12, a slit 13, a contacting portion 14, a guide portion 15, and a spring (bias means) 16. The slit 13 is disposed at the first counterweight portion 12 and the balance member 4c is connected to the slit 13 to be slidable. The contacting portion 14 protrudes from the balance member 4c in a direction parallel to the horizontal axis O2 to be slidably disposed inside the slit 13. The guide portion 15 is configured for moving the first counterweight portion 12 in the vertical direction after receiving a force generated when the contacting portion 14 is guided and moved in the slit 13 according to the rotation of the second arm mechanism 4. The spring 16 is configured to bias the first counterweight portion 12 downward in the vertical direction.

The first counterweight portion 12 is a plate-shaped weight formed from a metal material for example. A principle plane of the first counterweight portion 12 extends to be substantially orthogonal to the horizontal axis O2. That is, the first counterweight portion 12 is disposed to be substantially parallel to the rotation plane of the balance member 4c. The first counterweight portion 12 is attached to the support shaft 5 to be movable in the vertical direction by the guide portion 15 and a moving direction of the counterweight portion 12 is regulated. A contour shape of the counterweight portion 12 is substantially rectangular; however the first counterweight portion 12 only has to be covered by the cover portion 7 and movable in the vertical direction, the shape thereof is not limited.

The guide portion 15 is configured by an elongated slot 15a and a position-regulating projection 15b. The elongated slot 15a is formed by penetrating the counterweight portion 12 in a width direction thereof. The elongated slot 15a extends in the vertical direction, and the position-regulating projection 15b is fixed to the support shaft 5 to be inside the elongated slot 15a. In the example shown in FIG. 3, guide portions 15 are arranged in the upper end and the lower end of the first counterweight portion 12 respectively; however the present invention is not limited to the configuration if the movement of the first counterweight portion 12 can be smoothly regulated.

Figure 4:
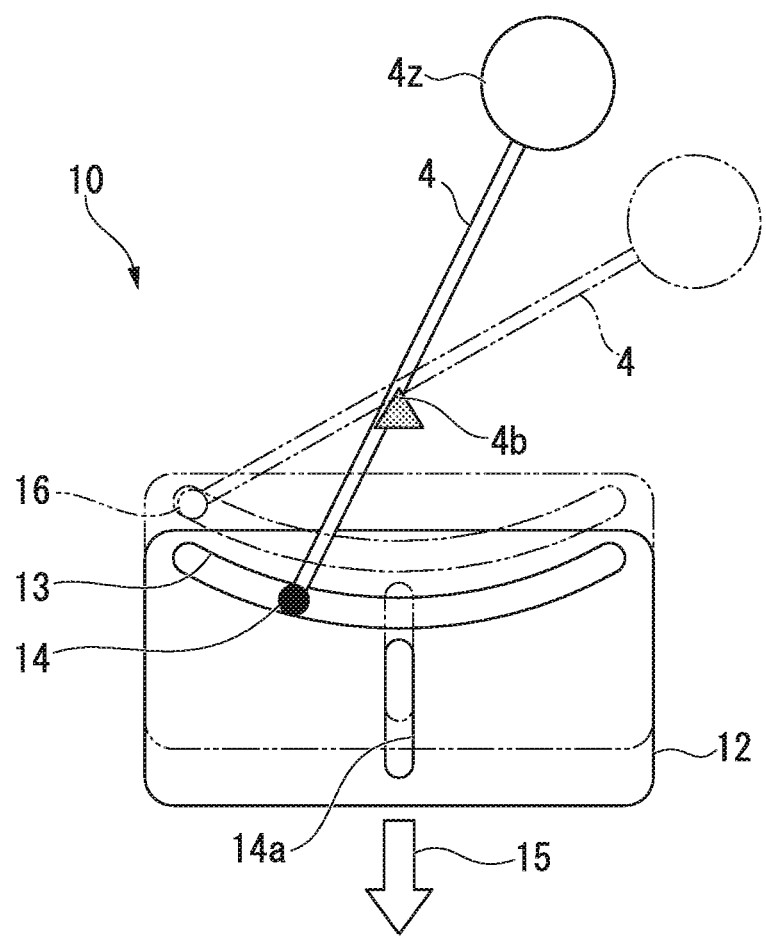
FIG. 4 is a schematic view showing the operation of the counterbalance mechanism of the medical device holding apparatus according to the present embodiment.
Figure 5:
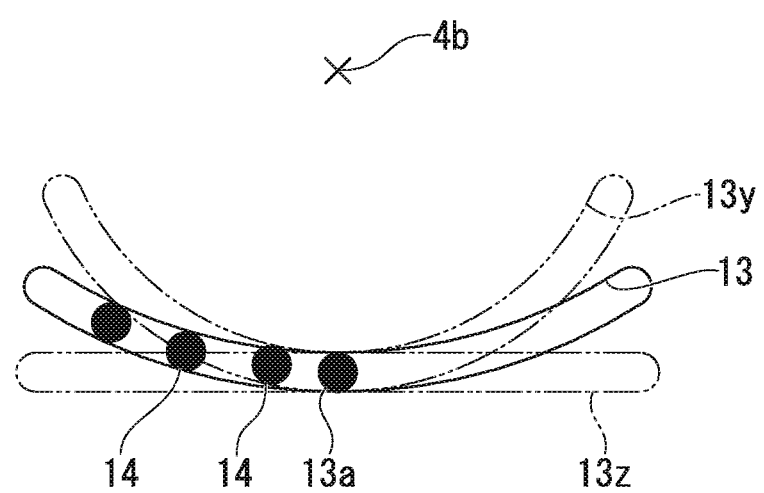
FIG. 5 is a front view showing a slit of the medical device holding apparatus according to the present embodiment.
Figure 6:
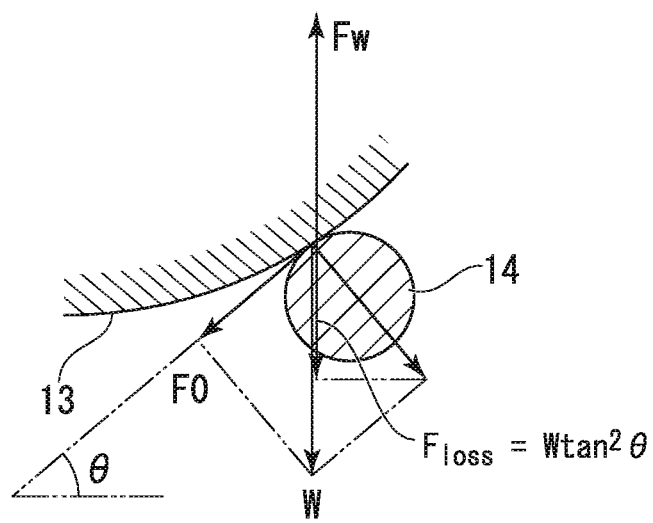
FIG. 6 is a front view showing a contacting state between the slit and a contacting portion of the medical device holding apparatus according to the present embodiment.

FIG. 4 is a schematic view showing an operation of the counterbalance mechanism 10 of the medical device holding apparatus 100 according to the present embodiment. FIG. 5 is a schematic view showing the slit 13 of the medical device holding apparatus 100 according to the present embodiment. FIG. 6 is a schematic front view showing a contacting state between the slit 13 and the contacting portion 14 of the medical device holding apparatus 100 according to the present embodiment. In the figures, a load (rotational momentum) at the second arm mechanism 4 is schematically shown as the numeral 4z.

The slit 13 is formed as a longitudinal slot penetrating the first counterweight portion 12 in the width direction thereof and having a center 13a positioned below the fulcrum 4b in the vertical direction, and the slit 13 extends toward the right and left sides of the center 13a.

As shown in FIG. 4 and FIG. 5, the slit 13 has a substantial same width over a whole length in the horizontal direction in which the slit 13 is bending, and the length of the slit 13 in the horizontal direction is determined corresponding to the rotation range of the second arm mechanism 4.

As shown in FIG. 4 and FIG. 5, in the slit 13, the center 13 positioned below the fulcrum 4b in the vertical direction is the lowest position, and the slit 13 is formed in a downward convex curved shape smoothly extending upward from the lowest center 13a toward two sides in the horizontal direction. As shown in FIG. 4 and FIG. 5, it is possible to form the slit 13 in a bilaterally symmetric shape with respect to the center 13a; however, the range of the slit 13 can be determined corresponding to the rotation range of the second arm mechanism 4 such that the contacting portion 14 is movable over the whole length of the slit 13. That is, it is possible to form the slit 13 in an asymmetric shape corresponding to the rotation range of the second arm mechanism 4.

As shown in FIG. 5, an upper contour line of the slit 13 is formed between a straight line 13z passing through the center 13a in the horizontal direction and a circular arc 13y passing through the center 13a while having the fulcrum 4b as a center. The center 13a is a point with which the contacting portion 14 comes in contact, when the second arm mechanism 4 is at a center position (for example, upward in the vertical direction) of the determined rotation range. At the same time, the center 13a is the point at which the bias force of the spring 16 is minimized.

Here, the circular arc 13y substantially has the same shape as a locus of a movement of the contacting portion 14 with the fulcrum 4b as the center. In the whole length of the slit 13, the straight line 13z is a shape when the load of the first counterweight portion 12 applies on the contacting portion 14.

The contacting portion 14 is formed to protrude from the balance member 4c so as to be orthogonal to the rotation plane thereof and positioned inside the slit 13. Even in a situation when the balance member 4c rotates, a contacting state between the contacting portion 14 and an upper slit surface in the slit 13 does not change and the contacting portion 14 can come in contact with the upper slit surface in a straight line shape substantially parallel to the horizontal axis O2. That is, as shown in FIG. 4 to FIG. 6, when viewed in the width direction of the first counterweight portion 12, the contacting portion 14 can come in contact with the slit 13 at a contact point. Accordingly, the contacting portion 14 is formed in a cylindrical shape such that the contacting state in the straight line shape does not change even if the contacting position with the slit 13 changes.

The contacting portion 14 can be formed as a cam follower such that a peripheral surface thereof is rotatable with the axis of the cylindrical shape. A diameter of the contacting portion 14 is substantially the same as the width of the slit 13 and it is preferable to determine the diameter of the contacting portion 14 such that the contacting portion 14 is movable in the slit 13. The contacting portion 14 is configured to transmit the load from the second arm mechanism 4 to the slit 13.

The spring (bias means) 16 is connected the lower end position of the first counterweight portion 12 and the support shaft 5, and the spring 16 is configured to bias the first counterweight portion 13 downward in the vertical direction. As described below, a bias force of the spring (bias means) 16 is determined such that the spring constant k is equal to a predetermined value.

Next, the shape of the slit 13 will be described.

As described above, the slit 13 with the bending shape has the shape between the straight line 13z passing through the center 13a in the horizontal direction and the circular arc with the fulcrum 4b as the center, and the slit 13 also has the shape which can be described as the downward convex parabolic curve.

Specifically, the slit 13 has the bending shape following an orbit of the contacting portion 14 which moves according to the movement of the second arm mechanism 4. The bending shape of the slit 13 is determined by the way shown as below.

Figure 7:
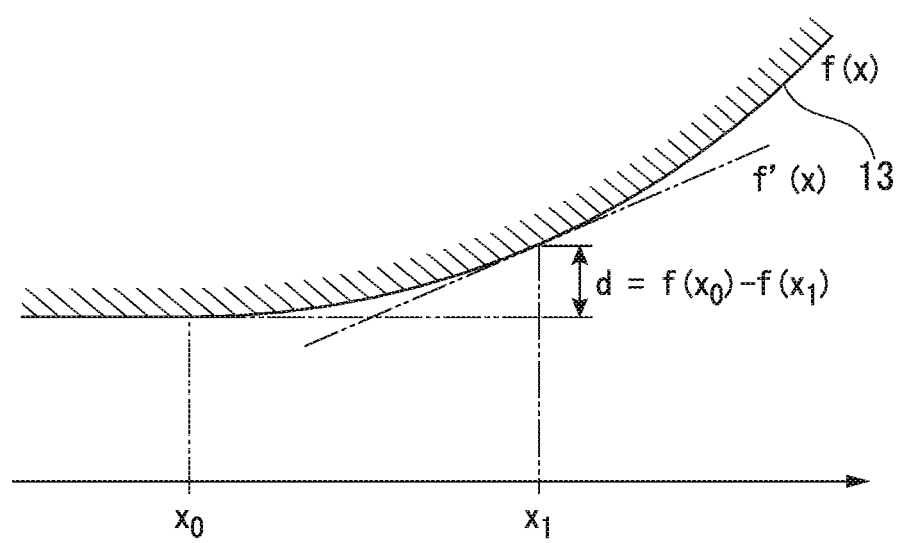
FIG. 7 is a schematic view showing a force with respect to the slit of the medical device holding apparatus according to the present embodiment.

FIG. 7 is a schematic view showing a force applied in the slit 13 of the medical device holding apparatus 100 according to the present embodiment.

In the slit 13 according to the present embodiment, as shown in FIG. 6, at the point at which the contacting portion 14 comes in contact with the slit 13, a force Fw which is shown as a load weight 4z in FIG. 4 and generated according to the weight of the medical devices supported by the first arm mechanism 3, the second arm mechanism 4, and the holding portion 2 is applied to the slit 13 from the contacting portion 14 upwardly in the vertical direction. An inclination of the slit 13 at the contacting point with the contacting portion 14 is described as an angle θ.

Here, as shown in FIG. 6, the movement range of the first counter weight portion 12 is regulated in the vertical direction such that a load W of the first counterweight portion 12 applies in the vertical downward direction; however, the contacting portion 14 contacts with the slit 13 at the point with an inclination of the angle θ such that the loss part of the load W in the inclination direction is described as a force F0, and a force $F_{loss}$ which is actually applied to the contacting portion 14 by subtracting the force F0 is determined by Equation 1 shown below.

$$F_{loss} = W \cdot \tan^2 \theta \qquad \text{[Equation 1]}$$

As shown in FIG. 7, supposing the slit 13 has the shape described by a function f(x) with respect to the horizontal direction x, a height when the contacting portion 14 moves from X0 to X1 differs by a value d in the height direction, which is determined by Equation 2 shown below.

$$d = f(x0) - f(x1) \qquad \text{[Equation 2]}$$

Accordingly, the length of the spring 16 with respect to the first counterweight portion 12 is changed and an assistance force $F_{assist}$ as a bias force kd proportional to the spring constant k is generated and applied.

Also, the inclination at the point x at which the contacting portion 14 contacts with the slit 13 is determined by Equation 3 shown below.

$$\tan \theta = f'(x) \qquad \text{[Equation 3]}$$

Accordingly, if the force $F_{loss}$ which is the loss part of the weight load of the first counterweight portion 12 is equal to the assistance force $F_{assist}$, the counterbalance mechanism 10 of the medical device holding apparatus 100 can sufficiently support the load weight 4z to keep balance. The function f(x) showing the slit shape is suitably determined based on Equation 4 shown below.

$$F_{assist} = F_{loss} \qquad \text{[Equation 4]}$$

Figure 8:
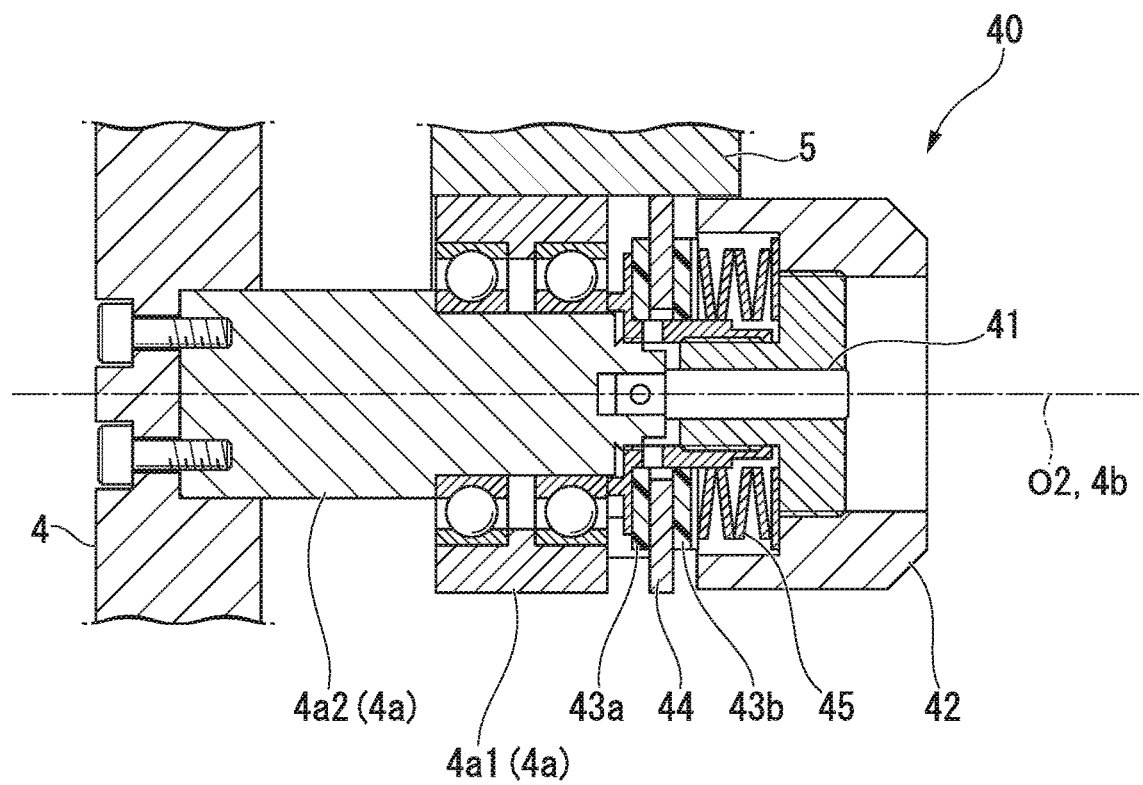
FIG. 8 is a cross section view showing a brake mechanism of the medical device holding apparatus according to the present embodiment.

FIG. 8 is a cross section view showing a braking mechanism 40 of the medical device holding apparatus 100 according to the present embodiment.

As shown in FIG. 8, the braking mechanism 40 is arranged at the distal end side of the bearing portion 4a which is configured by a ring-shaped portion 4a1 fixed to the support shaft 5 and a short-axis portion 4a2 fixed to the second arm mechanism 4.

Due to the braking mechanism 40, the rotation of the bearing portion 4a disposed at the proximal end of the second arm mechanism 4 with respect to the support shaft 5 around the horizontal axis O2 is suppressed. Due to the braking mechanism 40, a rotation load around the horizontal axis O2 is reduced by a friction condition, that is, a friction force generated at any rotation position of the second arm mechanism 4.

The braking mechanism 40 has a pressing ring 42, two friction plates 43a, 43b, a friction plate 44 sandwiched between the two friction plates 43a, 43b, and a disk spring 45. The pressing ring 42 is formed as a nut screwing to a screw 41 which is coaxially formed with the distal end of the short-axis portion 4a2. For example, the friction plates 43a, 43b can be formed from a resin, and the friction plate 44 can be formed from a metal material.

The braking mechanism 40 is configured to adjust the friction force between the friction plates 43a, 43b fixed to the short-axis portion 4a2 and the friction plate 44 fixed to the support shaft 5 by rotating the pressing ring 42, which is attached to the short-axis portion 4a2 so as to be freely rotatable, around the horizontal axis O2 to make the pressing ring 42 to move along the horizontal axis O2.

When the pressing ring 42 is screwed toward the second arm mechanism 4 side, the bias force of the disk spring 45 increases such that the friction force between the two friction plates 43a, 43b and the friction plate 44 sandwiched between the friction plates 43a, 43b is increased. On the other hand, when the pressing ring 42 is screwed back, the friction force is decreased. By suitably adjusting the friction force, the rotation force of the second arm mechanism 4 around the horizontal axis O2 with respect to the support shaft 5 can be suitably adjusted by the friction force. Also, the friction force corresponding to the bias force may be adjusted by increasing or reducing a number of the disk springs 45 of the braking mechanism 40.

Figure 9:
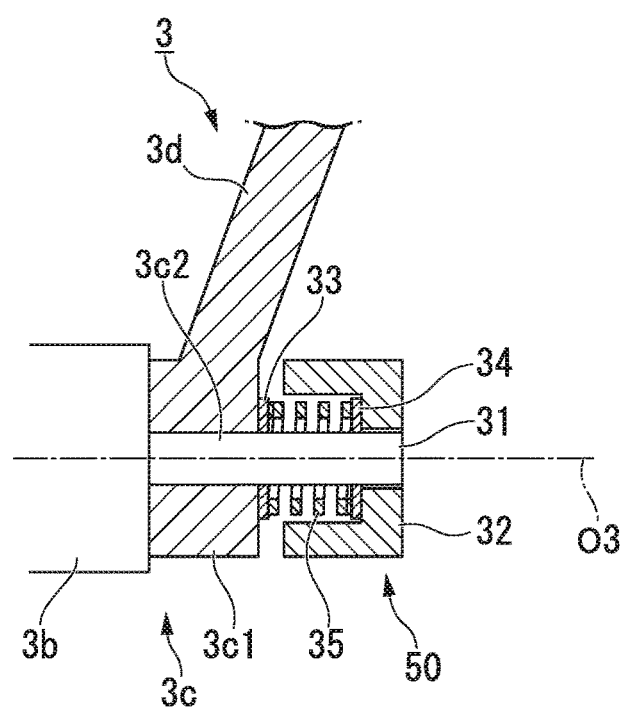
FIG. 9 is a cross section view showing a brake mechanism of the medical device holding apparatus according to the present embodiment.

FIG. 9 is a cross section view showing a braking mechanism 50 of the medical device holding apparatus 100 according to the present embodiment.

As shown in FIG. 9, at the proximal end side of the first arm mechanism 3, the braking mechanism 50 is arranged at the distal end side of the bearing portion 3c which is configured by a ring-shaped portion 3c1 fixed to the rotation portion 3b and a short-axis portion 3c2 fixed to the first extension portion 3d.

The braking mechanism 50 has a pressing ring 32, two friction plates 33, 34, and a disk spring 35. The pressing ring 32 is formed as a nut screwing to a screw 31 which is coaxially formed with the distal end of the short-axis portion 3c2.

Due to the braking mechanism 50, the first extension portion 3d can be held in a semifixed state with respect to the rotation portion 3b of the first arm mechanism 3 by the friction force, that is, the first extension portion 3d of the first arm mechanism 3 can be held at any rotation position around the axis O4 by the friction force. Also, the first extension portion 3d can be immediately rotated to be rearranged at a desired position by applying a force larger than the friction force to the first extension portion 3d.

When the pressing ring 35 is screwed toward the rotation portion 3b side, the bias force of the disk spring 35 increases such that the friction force between the rotation portion 3b and the first extension portion 3d is increased. On the other hand, when the pressing ring 35 is screwed back, the friction force is decreased. By suitably adjusting the friction force, the first extension portion 3d can be held at a suitable position. In this way, the friction force corresponding to the bias force may be adjusted by increasing or reducing a number of the disk springs 35 of the braking mechanism 50.

According to the medical device holding apparatus 100 according to the present embodiment, it is possible to arrange the first arm mechanism 3 and the second arm mechanism 4 by any angle and keep the load balance in a state in which the medical device is held by the holding portion 2.

Specifically, as shown in FIG. 4, when the load weight 4z of the medical device supported by the first arm mechanism 3, the second arm mechanism 4, and the holding portion 2 applies and the second arm mechanism 4 is moved to be at a predetermined angle, the second arm mechanism 4 is pivoted (rotated) around the fulcrum 4b as the center. At the same time, the contacting portion 14 is symmetrically rotated with the load weight 4z around the fulcrum 4b as the center.

At this time, when the rotation force with respect to the second arm mechanism 4 is regulated by the friction force from the braking mechanism 40, a differential force of the load weight 4z and the friction force applies to the slit 13 from the contacting portion 14 such that the first counterweight portion 12 receives a force in the vertical direction.

Accordingly, the first counterweight portion 12 regulated by the guide portion 15 moves until a vertical position defined by the moving locus of the contacting portion 14 and the shape of the slit 13.

At the same time, due to the movement of the first counterweight portion 12, the first counterweight portion 12 receives the bias force from the expanded or pressed spring 16.

Since it is possible to balance the differential force between the load weight 4z and the friction force, and a sum force of the weight W of the first counterweight 12 and the bias force of the spring 16 by determining the friction force of the braking mechanism 40 and the bias force of the spring 16 in advance, the second arm mechanism 4 can be kept in balance to standstill at any position such that the second arm mechanism 4 can balance the load weight 4z in any orientation and maintain the orientation.

At this time, according to the shape of the slit 13 described above, when the contacting portion 14 moves, a change amount of the load weight 4z due to the movement of the contacting portion 14 is canceled by a change amount of the bias force from the spring 16 due to the movement of the first counterweight portion 12 in the height direction, and the load balance is kept regardless of the angle of the second arm mechanism 4.

Here, as shown in FIG. 5, when the upper contour line of the slit 13 is set to be the straight line 13z passing through the center 13a and extending in the horizontal direction, once the contacting portion 14 moves, over the whole movement range of the contacting portion 14, the force by the load weight 4z applies from the contacting portion 14 to the slit 13 such that the total weight of the first counterweight portion 12 can be loaded by the second arm mechanism 4; however, it is necessary to set the movement range of the first counterweight portion 12 to be large since the first counterweight portion 12 has to move a distance equal to the change amount of the height of the contacting portion 14.

As shown in FIG. 5, when the upper contour line of the slit 13 is set to be the circular arc 13y passing through the center 13a and having the fulcrum 4b as the center, once the contacting portion 14 moves, over the whole movement range of the contacting portion 14, the force by the load weight 4z does not apply from the contacting portion 14 to the slit 13 such that the first counterweight portion 12 does not move in the vertical direction. Since the contacting surface between the contacting portion 14 and the slit 13 is inclined, the force increases/decreases according to the contacting positions so as to make it difficult to balance the force at some contacting position and maintain the orientation of the second arm mechanism 4. Accordingly, it is necessary to increase the weight of the first counterweight portion 12.

According to the medical device holding apparatus 100 according to the present embodiment, the slit 13 is formed in the shape described above such that the change (loss) of the load from the weight of the first counterweight portion 12 corresponding to the inclination amount of the slit 13 occurs together with the change of the contacting position of the contacting portion 14 with respect to the slit 13; however, the loss of the weight of the first counterweight portion 12 corresponding to the inclination amount of the slit 13 can be compensated corresponding to the position of the first counterweight portion 12 in the height direction (vertical displacement) by connecting the spring 16 to the first counterweight portion 12 to apply the bias force corresponding to the position in the height direction. Accordingly, the load weight 4z and the first counterweight portion 12 can be balanced by gravity regardless of the angle of the second arm mechanism 4.

According to the present embodiment, it is possible to reduce the weight of first counterweight portion 12 based on the following conditions shown as Equations 5 and 6.

INITIAL TENSION OF SPRING 16=NECESSARY GRAVITY OF FIRST COUNTERWEIGHT 12 [Equation 5]

SPRING CONSTANT K=GRAVITY LOSS RATIO OF FIRST COUNTERWEIGHT 12 [Equation 6]

The reason is that in the applied load generated from the weight of the first counterweight portion 12, the loss part due to the position of the contacting portion 14 is in proportion to the weight of the first counterweight portion 12 and determined by the contacting angle θ at the slit 13.

Second Embodiment

Next, a second embodiment of the medical device holding apparatus of the present invention will be described with reference to the figures.

Figure 10:
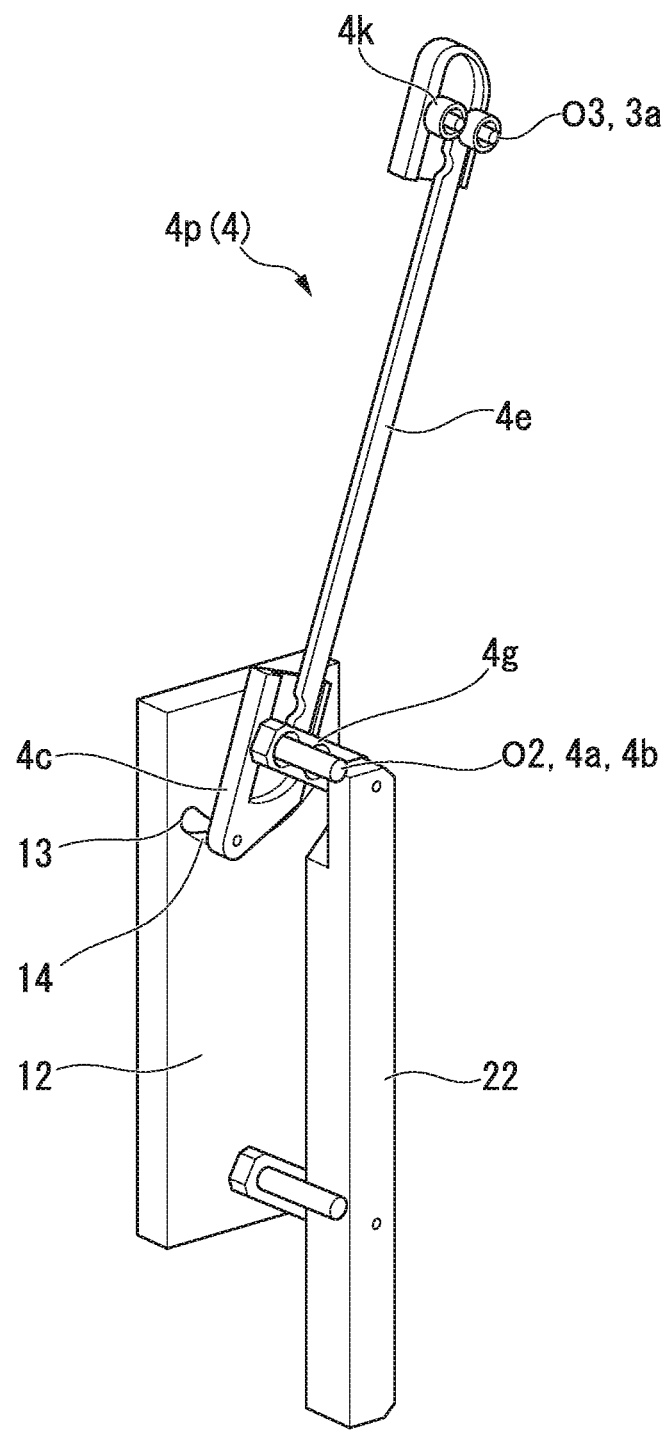
FIG. 10 is a perspective view showing an operation of a counterbalance mechanism of a medical device holding apparatus according to a second embodiment of the present invention.
Figure 11:
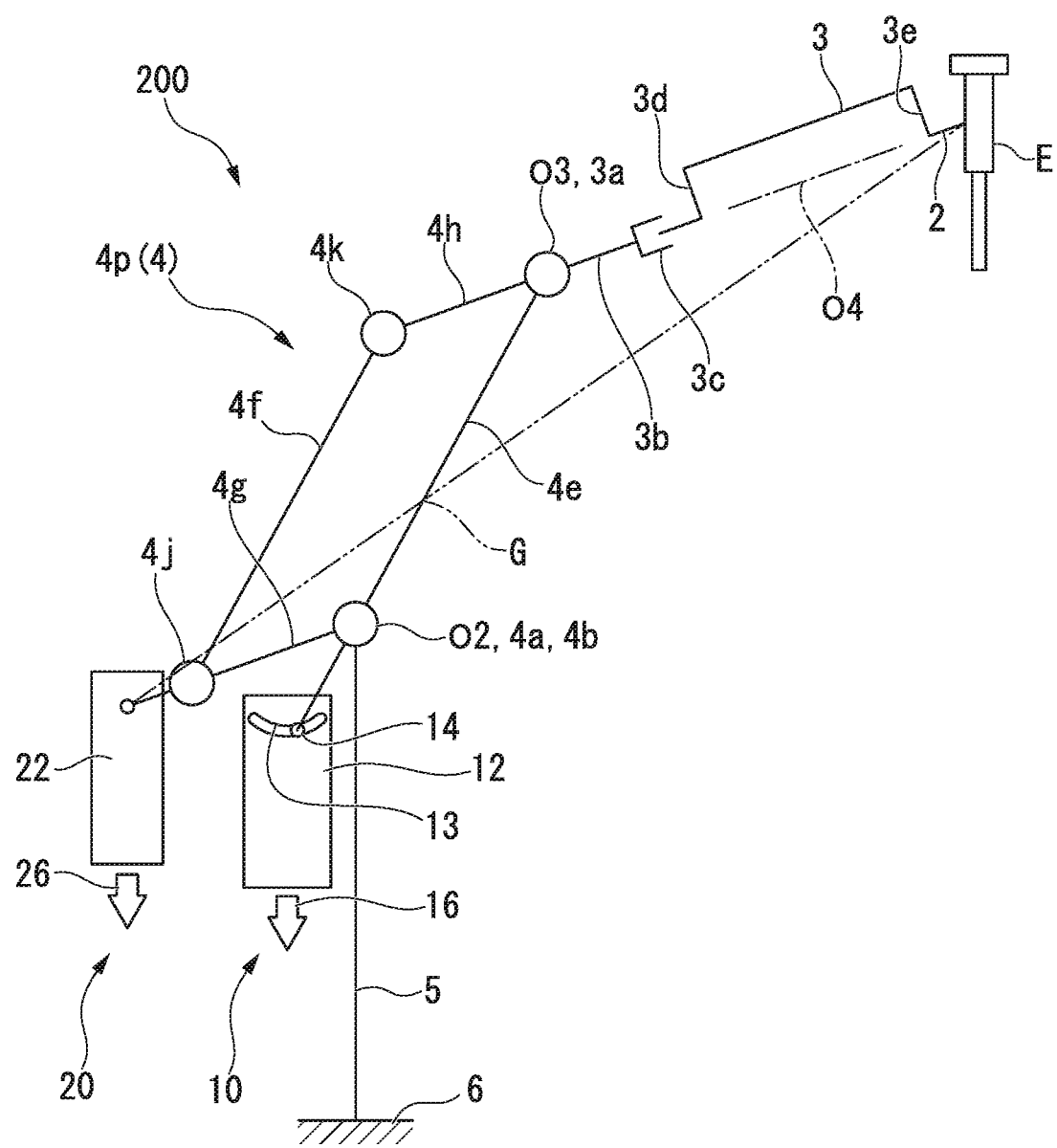
FIG. 11 is a schematic view showing the operation of the counterbalance mechanism of a medical device holding apparatus according to the present embodiment.

FIG. 10 is a perspective view showing an operation of a counterbalance mechanism according to the present embodiment. FIG. 11 is a schematic view showing the operation of the counterbalance mechanism according to the present embodiment. In the present embodiment, configurations corresponding to those described in the first embodiment will be denoted by the same reference numerals, and part of the description thereof will be omitted as appropriate.

As shown in FIG. 10, the medical device holding apparatus 200 according to the present embodiment has a base 6 which is movable on the floor or the like by a plurality of casters 6a. A bearing portion 5a is arranged in the base 6 and for example, a lower end of a support arm (support shaft) 5 which is freely rotatable around the vertical axis O1 with respect to the base 6 is supported by the bearing portion 5a. A bearing portion (fulcrum) 4a is arranged at an upper end of the support arm 5. The rotation axis (horizontal axis) O2 which is orthogonal to the vertical axis O1 is arranged in the bearing portion 4a, and a first arm (arm) 4e as the second arm mechanism 4 which is a freely pivotable (rotatable) member around the rotation axis O2 is attached to the bearing portion 4a.

The bearing portion 4a is arranged at one end of the first arm (arm) 4e and the bearing portion 3a is arranged at the other end thereof. One end of an arm (third arm) 4g is connected to the bearing portion 4a so as to be rotatable around the rotation axis O2 being through the bearing portion 4a. One end of an arm (fourth arm) 4h is connected to the bearing portion 3a so as to be rotatable around the rotation axis (horizontal axis) O3 being parallel to the rotation axis O2 and being through the bearing portion 3a. It is suitable to arrange the bearing portion 4a at the lower end of the arm 4e for achieving the miniaturization.

Furthermore, bearing portions 4j, 4k are arranged at the other end of the arm 4g and the arm 4h respectively. Two ends of an arm (second arm) 4f are connected to these bearing portions 4j, 4k respectively, wherein the arm 4f is rotatable around the axes O2, O3 being through the bearing portions 4j, 4k respectively, and the arm 4f is parallel to the arm (first arm) 4e. Accordingly, a parallelogram link mechanism 4p equivalent to a balance means of the medical device holding apparatus 200 is configured by the four arms 4e, 4f, 4g, 4h and the four bearing portions 4a, 3a, 4k, 4j.

In the arm 4e, part at the opposite side of the bearing portion 3a is extended more outwardly from the parallelogram link mechanism 4p than the bearing portion 4a. In the arm 4g, part at the opposite side of the bearing portion 4a is extended more outwardly from the parallelogram link mechanism 4p than the bearing portion 4j. In the arm 4h, part at the opposite side of the bearing portion 4k is extended more outwardly from the parallelogram link mechanism 4p than the bearing portion 3a.

Compared with the arms 4g, 4h, it is preferable that the arms 4e, 4f are formed to be elongated. The arm 4e is preferable to be formed with a wider width than the other arms 4f, 4g, 4h such that the operation of the parallelogram link mechanism 4p can be performed within the degree of the width dimension of the arm 4e.

The arm 4e is configured to be corresponding to the second arm mechanism 4 according to the first embodiment described above.

One bearing portion 3a of the parallelogram link mechanism 4p is connected by the rotation portion 3b, and a bearing portion 3c is arranged at the rotation portion 3b, wherein the bearing portion 3c has the axis O4 orthogonal to the axis O3 of the bearing portion 3a. A proximal end (base end) of an elongated arm (first arm mechanism) 3 as the supporting means of the medical device is supported at the bearing portion 3c, and the proximal end of the support arm 3 and the arm 4h are integratedly connected.

The arm 3 has the first extension portion 3d such that the proximal end side of the arm 3 separates from the axis 4. Accordingly, the proximal end of the arm 3 and the arm 4h are disposed on the same axis O4, while the arm 3 and the arm 4h are arranged to be parallel to the axis O4. A distal end (front end) of the arm 3 has the second extension portion 3e which is bent to make the arm 3 to approach the axis O4 until the distal end of the arm 3 is on the axis O4.

The holding portion 2 for holding the medical device is arranged at the distal end of the arm 3. The holding portion 2 is supported by the arm 3 due to the rotation-force adjustment portion which is rotatable around the axis O4 as the center. Furthermore, the holding portion 2 is rotatable together with the held medical device around the axes O5, O6 as the center which are orthogonal to the axis O4, and the force necessary for the rotation is adjusted by the rotation-force adjustment portion.

On the other hand, the other end of the arm 4g being extended more outwardly from the parallelogram link mechanism 4p than the bearing portion 4j on the diagonal line of the bearing portion 3a described above is connected with a second counterweight portion 22 as the counterbalance mechanism 20. The second counterweight portion 22 is configured to have a predetermined weight for cancelling a moment of inertia (rotation) generated around the axis O3 by the heavy load such as the medical device and the like supported by the holding portion 2 to balance the orientation of the medical device holding apparatus 200. The weight of the second counterweight portion 22 is suitably selectable according to the heavy load and the distance between the heavy load and the axis O2.

Furthermore, for example, an electro-magnetic brake (electro-magnetic clutch) configured to electrically regulate the rotation of the support shaft 5 with respect to the base 6 around the axis O1 may be disposed at the bearing portion 5a.

The braking mechanism 40 configured to regulate the rotation of the arm 4e around the axis O2 is arranged at the bearing portion 4a. A braking mechanism having the same configuration as that of the braking mechanism 40 is arranged at the bearing portion 3a for regulating the rotation of the arm 4h around the axis O3. The braking mechanism 50 configured to regulate the rotation of the arm 3 around the axis O4 is arranged at the bearing portion 3c. Furthermore, a braking mechanism configured to regulate the rotation of the arm 3 is arranged at the holding portion 2.

Either of these braking mechanism 40 and braking mechanism 50 has the corresponding configuration as the braking mechanism 40 and the braking mechanism 50 according to the first embodiment.

On the other hand, the proximal end of the arm 4e being extended more outwardly from the parallelogram link mechanism 4p than the bearing portion 4a on the diagonal line of the bearing portion 4k described above is connected with the first counterweight portion 12 as the counterbalance mechanism 10. The first counterweight portion 12 is configured to have a predetermined weight for cancelling a moment of inertia (rotation) generated around the axis O2 by the heavy load such as the medical device and the like supported by the holding portion 2 to balance the orientation of the medical device holding apparatus 200.

In FIG. 10 and FIG. 11, the counterbalance mechanism 10 is omitted.

Figure 12:
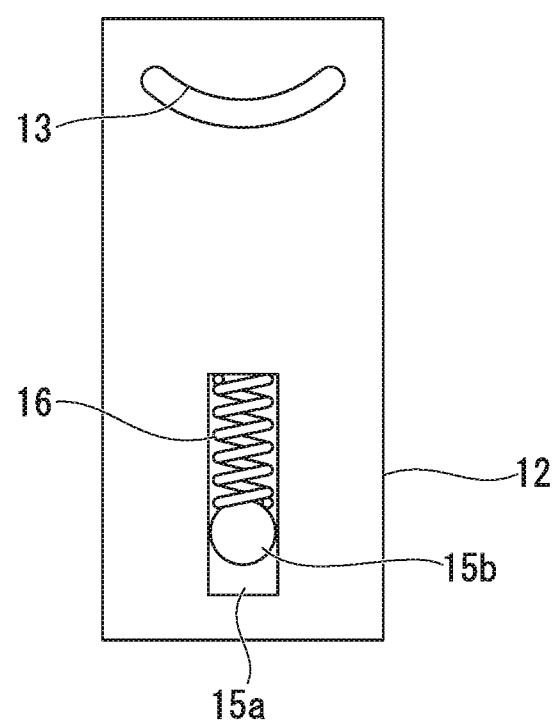
FIG. 12 is a front view showing an example of a counterbalance portion of a medical device holding apparatus according to another embodiment of the present invention.

As shown in FIG. 10 to FIG. 12, the counterbalance mechanism 20 has the second counterweight portion 22 and a spring (bias means) 26 configured to bias the second counterweight portion 26 to be downward in the vertical direction.

The second counterweight portion 22 is attached to the arm 4g. The contour shape of the second counterweight portion 22 can be substantially rectangular; however, if the second counterweight portion 22 can be accommodated in the cover portion 7 and can move in the vertical direction, the shape is not limited thereto.

The proximal end side of the arm 4e, the counterbalance mechanism 10, the counterbalance mechanism 20, and the support shaft 5 are accommodated in the tubular cover portion 7 standing on the base 6. It is possible to arrange the cover portion at the arm 4e for accommodating the arms 4f, 4g, 4h inside.

As same as the first embodiment, the shape of the slit 13 is determined in consideration of the weight of the medical device E and the like supported by the first arm mechanism 3, the second arm mechanism 4, and the holding portion 2, the load weight 4z generated by the weight of the second counterweight portion 22, the friction force of the braking mechanism 40, and the force generated in the counterbalance mechanism 10 corresponding to these forces.

According to the medical device holding apparatus 200 according to the present embodiment, the slit 13 is formed in the predetermined shape such that the change (loss) of the load from the weight of the first counterweight portion 12 corresponding to the inclination amount of the slit 13 occurs together with the change of the contacting position of the contacting portion 14 with respect to the slit 13, the loss of the weight of the first counterweight portion 12 corresponding to the inclination amount of the slit 13 can be compensated corresponding to the position of the first counterweight portion 12 in the height direction (vertical displacement) by connecting the spring 16 to the first counterweight portion 12 to apply the bias force corresponding to the position in the height direction.

As shown in FIG. 11, a center of gravity with respect to the load weight 4z is coincided with the arm 4e.

Accordingly, it is possible to balance the load weight 4z and each of the first counterweight portion 12 and the second counterweight portion 22 by the gravity, keep balance of the orientation of the medical device holding apparatus 200 by the counterbalance mechanism 20, and keep balance of the position of medical device holding apparatus 200 by the counterbalance mechanism 10 regardless of the transformation state of the parallelogram link mechanism 4p and the angle of the arm 4g and the arm 4e so as to freely move the position of the medical device E in the three-dimension space while maintaining the orientation thereof. Accordingly, it is possible to achieve both goals of reducing the space of the movable range of the counterweight portion 12, 22 and reducing the weight thereof for downsizing and lightening.

In the present embodiment, it is possible to reduce the weight of first counterweight portion 12 based on the following conditions shown as the Equations 5 and 6.

$$\text{INITIAL TENSION OF SPRING } 16 = \text{NECESSARY GRAVITY OF FIRST COUNTERWEIGHT } 12 \quad \text{[Equation 5]}$$

$$\text{SPRING CONSTANT } K = \text{GRAVITY LOSS RATIO OF FIRST COUNTERWEIGHT } 12 \quad \text{[Equation 6]}$$

Furthermore, the lengths of each arm in the parallelogram link mechanism 4p are suitable to fulfill the following conditions. Specifically, it is suitable that the arm 3 has a length of approximately 600 millimeters, each of the arms 4e and 4f has a length of approximately 550 millimeters, each of the arms 4g and 4h has a length of approximately 40 millimeters, and the distance from the axis O2 to the load position 24 of the counterweight portion is approximately 80 millimeters.

In the embodiments described above, the spring 16 is connected to the lower end of the counterweight portion 12; however, as shown in FIG. 13, it is possible to arrange the spring 16 inside the elongated slot 15a of the guide portion 15. According to this configuration, the spring 16 is accommodated in the elongated slot 15a in a manner that the expanding/contracting direction of the spring 16 coincides with the extending direction of the elongated slot 15a and the end portion of the spring 16 engages with the end portion of the elongated slot 15a and the position-regulation protrusion 15b so as to save space at the lower end side of the counterweight portion 12 for furtherly achieving the miniaturization of the apparatus.

In a situation of a scope holder having arms with the lengths described above, comparing to the counterweight portion 12 having a weight of 30 kilograms to 50 kilograms generally, in the medical device holding apparatus 200 having the same movable range according to the present embodiment, it is possible to reduce weight of the apparatus by 90%.

Either, in the medical device holding apparatus 200 according to the present embodiment, it is possible to enlarge the movable range of the holding portion 2 if the weight of the apparatus is the same.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A medical device holding apparatus comprising:
   a first arm mechanism having a holding portion configured to hold a medical device;
   a second arm mechanism connected to the first arm mechanism so as to make the first arm mechanism to be rotatable;

a base connected to the second arm mechanism so as to make the second arm mechanism to be rotatable, the base having a support shaft standing in a vertical direction; and a first counterweight connected to a proximal end portion of the second arm mechanism, wherein the second arm mechanism has a fulcrum connected to the support shaft, the second arm mechanism being rotatable around the fulcrum, and wherein the first counterweight has:
- a slit connected to the proximal end portion of the second arm mechanism, the slit being configured to guide the proximal end portion of the second arm mechanism when the second arm mechanism is rotated around the fulcrum; and
- a guide configured to move the first counterweight in the vertical direction after the guide receives a force generated when the proximal end portion of the second arm mechanism is guided and moved in the slit.

2. The medical device holding apparatus according to claim 1, wherein the slit is formed in a downward convex curved shape.

3. The medical device holding apparatus according to claim 1 further comprising a second counterweight different with the first counterweight, wherein the second arm mechanism includes:
- a first arm having a distal end connected to the first arm mechanism and a proximal end connected to the first counterweight;
- a second arm disposed parallelly to the first arm;
- a third arm having a distal end connected to the first arm and a proximal end connected to the second counterweight, the third arm being connected to the second arm; and
- a fourth arm having a distal end connected to the first arm and a proximal end connected to the second arm, the fourth arm being parallel to the third arm.

4. The medical device holding apparatus according to claim 1, wherein the fulcrum has a brake mechanism configured to suppress rotation of the second arm mechanism.

5. The medical device holding apparatus according to claim 4 further comprising a spring configured to bias the first counterweight downward in the vertical direction, wherein the shape of the slit is determined such that a bias force of the spring, a rotation-suppressing force of the brake mechanism with respect to the second arm mechanism, and a force generated at the slit when the slit guides the proximal end portion of the second arm mechanism are balanced.

6. The medical device holding apparatus according to claim 1, wherein the proximal end portion of the second arm mechanism has a contacting portion, the contacting portion contacting with the slit in a point-contact manner in a guide direction in which the proximal portion of the second arm mechanism is guided.

* * * * *